(12) United States Patent
Hattori et al.

(10) Patent No.: US 6,884,416 B2
(45) Date of Patent: Apr. 26, 2005

(54) STABLE PQQ-DEPENDENT GLUCOSE DEHYDROGENASE COMPOSITION

(75) Inventors: Shizuo Hattori, Tsuruga (JP); Atsushi Sogabe, Tsuruga (JP); Seiji Takeshima, Tsuruga (JP); Yoshihisa Kawamura, Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 82 days.

(21) Appl. No.: 09/781,703

(22) Filed: Feb. 12, 2001

(65) Prior Publication Data

US 2001/0021523 A1 Sep. 13, 2001

(30) Foreign Application Priority Data

Feb. 17, 2000 (JP) ........................................ 2000-039857

(51) Int. Cl.$^7$ ............................ C12N 9/02; C12N 9/04; C12N 9/06; C12N 9/08
(52) U.S. Cl. ...................... 424/94.4; 424/94.3; 435/189; 435/190; 435/191; 435/192
(58) Field of Search ................................ 424/94.3, 94.4; 435/189, 190, 191, 192

(56) References Cited

FOREIGN PATENT DOCUMENTS

JP          09-140378          6/1997

OTHER PUBLICATIONS

Kilty et al., "Reconstitution of Glucose Dehydrogenases Using Synthetic Methoxatin," *Archives of Biochemistry and Biophysics, 218* (2), 623–625 (1982).

Geiger et al., "Reversible Thermal Inactivation of the Quinoprotein Glucose Dehydrogenase from *Acinetobacter calcoaceticus,*" *Biochem. J., 261*, 415–421 (1989).

Sode et al., "Preparation of Lyophilized Pyrroloquinoline Quinone Glucose Dehydrogenase Using Trehalose as an Additive," *Biotechnology Techniques, 11* (8), 577–580 (Aug. 1997).

Ameyama, "Enzymic Microdetermination of D–Glucose, D–Fructose, D–Gluconate,2–Keto–D–Gluconate, Aldehyde, and Alcohol with Membrane–Bound Dehydrogenases," *Methods in Enzymology, 89*,20–29 (1982).

*Primary Examiner*—Irene Marx
(74) *Attorney, Agent, or Firm*—Leydig, Voit & Mayer, Ltd.

(57) ABSTRACT

The present invention provides a stable lyophilized PQQ-dependent glucose dehydrogenase composition comprising a PQQ-dependent glucose dehydrogenase together with (i) at least one compound selected from the group consisting of aspartic acid, glutamic acid, α-ketoglutaric acid, malic acid, α-ketogluconic acid, α-cyclodextrin and their salts and (ii) an albumin.

14 Claims, No Drawings

STABLE PQQ-DEPENDENT GLUCOSE DEHYDROGENASE COMPOSITION

TECHNICAL FIELD

The present invention relates to a stable composition comprising a PQQ-dependent glucose dehydrogenase.

A PQQ-dependent glucose dehydrogenase (glucose dehydrogenase being hereinafter sometimes referred to as GDH) is suitable for highly sensitive determination of glucose since it is capable of reducing an artificial electron acceptor by irreversible reaction.

BACKGROUND ART

The chemical structure of PQQ (pyrroloquinoline quinone) was identified in 1979 as the third coenzyme of dehydrogenases. The presence of PQQ is confirmed mainly in dehydrogenases of many organisms, typically methanol dehydrogenase of methanol assimilating bacteria, alcohol dehydrogenase of Acetobacteria, and GDH.

Since these dehydrogenases are capable of reducing an artificial electron acceptor, they are detectable by visible light with high sensitivity, when using a dye such as nitro blue tetrazolium. Also, these dehydrogenases undergo one-way reaction, unlike AND-dependent dehydrogenases which undergo equilibrium reaction. For these reasons, these dehydrogenases are reported to be very useful for microdetermination of a compound (Methods Enzymol. vol. 89, 20 (1982)).

The most useful enzyme having PQQ as a prosthetic group is PQQ-dependent GDH, which can be utilized for determination of blood sugar. The PQQ-dependent GDH has wide applications, for example, as a dry reagent immobilized on a membrane for color reaction or as a sensor immobilized on a chip, besides the ordinary application as a biochemical reagent. As compared with glucose oxidase or NAD(P)-dependent GDH which exert the same action on glucose, the PQQ-dependent GDH is unsusceptible to dissolved oxygen, and undergoes a simple reaction which can be conducted with a simple, inexpensive device.

On the other hand, the PQQ-dependent GDH is known to have a lower stability than glucose oxidase, hexokinase or NAD(P)-dependent GDH used in glucose measurement. The mechanism of inactivation is specifically described in, for example, Biochem. J., 261,415 (1989). As to stabilization of the PQQ-dependent GDH, for instance, Arch. Biochim. Biophys., 218,623 (1982) discloses use of PQQ, and Japanese Unexamined Patent Publication No. 1997-140378 teaches combined use of calcium ions, and at least one of glutamic acid, glutamine and lysine, for instance.

However, most of the reports on stabilization of the PQQ-dependent GDH are concerned with a stabilizing method performed in a liquid, for example, a buffer solution. In view of the fact that enzymes as materials for diagnostic reagents are marketed generally in powder form (occasionally in glandular form), the reported methods are not always applicable to stabilization of enzyme products. Further, there are compounds effective for stabilization in liquid form, but liable to absorb moisture when mixed with a protein. It is often the case that such compounds rather lower the stability. In other words, there has been no report on a satisfactory method for stabilizing a PQQ-dependent GDH in the form of a powder, such as a lyophilizate.

DISCLOSURE OF THE INVENTION

The present inventors conducted extensive research to achieve the above object, and found that a PQQ-dependent GDH can be stabilized when it is made to coexist with (i) at least one compound selected from the group consisting of aspartic acid, glutamic acid, α-ketoglutaric acid, malic acid, α-ketogluconic acid, α-cyclodextrin and their salts and (ii) an albumin, for lyophilization. The present invention has been accomplished based on this finding.

The present invention provides the following:

(1) A stable lyophilized PQQ-dependent glucose dehydrogenase composition comprising a PQQ-dependent glucose dehydrogenase together with (i) at least one compound selected from the group consisting of aspartic acid, glutamic acid, α-ketoglutaric acid, malic acid, α-ketogluconic acid, α-cyclodextrin and their salts and (ii) an albumin.

(2) The composition according to the item (1), which further contains a buffer.

(3) A method for stabilizing a PQQ-dependent glucose dehydrogenase, wherein the PQQ-dependent glucose dehydrogenase is made to coexist with (i) at least one compound selected from the group consisting of aspartic acid, glutamic acid, α-ketoglutaric acid, malic acid, α-ketogluconic acid, α-cyclodextrin and their salts and (ii) an albumin.

(4) The method according to the item (3), wherein the PQQ-dependent glucose dehydrogenase is made to coexist further with a buffer.

One embodiment of the present invention is a stable lyophilized PQQ-dependent GDH composition comprising a PQQ-dependent GDH together with stabilizers, i.e., (i) at least one compound selected from the group consisting of aspartic acid, glutamic acid, α-ketoglutaric acid, malic acid, α-ketogluconic acid, α-cyclodextrin and their salts and (ii) an albumin.

The GDH for use in the present invention is an enzyme classified under EC1.1.99.17 and capable of catalyzing the following reaction:

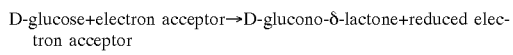

D-glucose+electron acceptor→D-glucono-δ-lactone+reduced electron acceptor

For use in the present invention, the PQQ-dependent GDH may be one collected from bacteria such as genera *Acinetobacter, Pseudomonas* and *Gluconobacter*, one collected from microorganisms such as *Escherichia coli*, or one produced from recombinant microorganisms obtained by incorporating genes of these PQQ-dependent GDHs into other microorganisms. Also, a genetically modified PQQ-dependent GDH can be used. It is preferred to use a PQQ-dependent GDH produced from a recombinant microorganism of an Acinetobacter-derived soluble GDH, or a gene-modified product obtained therefrom.

The GDH content of the lyophilized composition is varied depending on the origin of the enzyme, but a GDH content of about 5 to 50% by weight is usually preferred. The GDH content calculated as enzyme activity is preferably 100 to 2000 U/mg.

Salts of aspartic acid, glutamic acid, α-ketoglutaric acid, malic acid and α-ketogluconic acid for use in the invention include, but are not limited to, sodium, potassium, ammonium, calcium and magnesium. The at least one member selected from the above compounds, salts thereof and α-cyclodextrin is added preferably in an amount of 1 to 90% by weight. These substances may be used either singly or in combination.

The buffer for use in the lyophilized composition is not limited, and may be Tris buffer, phosphate buffer, borate buffer, Good's buffer or the like. The buffer is adjusted to a pH of about 5.0 to 9.0 according to the purpose of use.

The buffer content of the lyophilized composition is not limited, but is preferably at least 0.1% by weight, in particular 0.1 to 30% by weight.

Albumins usable in the present invention include, for example, bovine serum albumin (BSA) and ovalbumin (OVA). BSA is particularly preferable. The albumin content is preferably 1 to 80% by weight, more preferably 5 to 70% by weight.

The lyophilized composition of the invention may further contain other stabilizer(s) or the like in such an amount that does not adversely affect the reaction of GDH.

The stabilizers for use in the present invention may be mixed with the GDH by any process without limitation. For example, the stabilizers may be added to a buffer containing the GDH; or the GDH may be added to a buffer containing the stabilizers; or the GDH and the stabilizers may be added to a buffer at the same time.

The method for lyophilization is not limited and may be a routine one. The composition of the invention is not limited to a lyophilizate, and may be a solution obtained by redissolving the lyophilizate.

According to the present invention, (i) at least one compound selected from the group consisting of aspartic acid, glutamic acid, α-ketoglutaric acid, malic acid, α-ketogluconic acid, α-cyclodextrin and their salts and (ii) an albumin, are added to a PQQ-dependent glucose dehydrogenase to obtain a lyophilized glucose dehydrogenase which is stable, has good handling properties, and withstands long-term storage.

In the present invention, the GDH activity is determined with the following reagents and under the following conditions:
<Reagents>
50 mM PIPES buffer (pH 6.5)
0.2 mM PMS
0.2 mM NTB
30.6 mM Glucose
0.19% Triton X-100
<Measurement conditions>
3 ml of the mixture of the above reagents was preliminarily heated at 37° C. for about 5 minutes, and 0.1 ml of an enzyme solution was added. After gentle mixing, the absorbance at 570 nm was recorded for 5 minutes using a spectrophotometer maintained at 37° C., with water as a control. Thereafter, the absorbance change per minute was calculated from the linear part of the obtained absorbance curve. In a blank test, distilled water, in place of the enzyme solution, was added to the reagent mixture, and the absorbance change was determined in the above manner. The enzyme quantity capable of forming ½ μmol of diformazan is taken as 1 unit (U).

BEST MODE FOR CARRYING OUT THE INVENTION

The following examples are provided to illustrate the present invention in further detail, and are not intended to limit the scope of the present invention.

EXAMPLE 1

A soluble PQQ-dependent glucose dehydrogenase derived from *Acinetobacter calcoaceticus* NCIMB11517 was dissolved in a 20 mM K-phosphate buffer (pH 7.0). To the solution, each of the additives shown in Table 1 was separately added, followed by lyophilization. The obtained lyophilizates were allowed to stand at room temperature for 60 minutes, and then stored at 37° C. for 1 week. Thereafter, the lyophilizates were redissolved to measure the enzyme activity. Table 1 shows the residual enzyme activity (%), relative to the enzyme activity immediately after lyophilization, which is taken as 100% residual activity.

TABLE 1

| | Additive | Residual activity (%) |
|---|---|---|
| 1 | BSA 50% | 59 |
| 2 | Glutamic acid 50% | 62 |
| 3 | α-Cyclodextrin 50% | 57 |
| 4 | BSA 30% + glutamic acid 30% | 88 |
| 5 | BSA 30% + α-cyclodextrin 30% | 77 |
| 6 | BSA 30% + aspartic acid 30% | 84 |
| 7 | BSA 30% + α-ketoglutaric acid 30% | 85 |
| 8 | BSA 30% + α-ketogluconic acid 30% | 78 |
| 9 | BSA 30% + malic acid 30% | 85 |

Table 1 reveals that the stability of the lyophilizates was improved by the combined use of BSA and one of glutamic acid, α-cyclodextrin, aspartic acid, α-ketoglutaric acid and α-ketogluconic acid.

EXAMPLE 2

A soluble PQQ-dependent glucose dehydrogenase derived from *Acinetobacter calcoaceticus* NCIMB11517 was dissolved in a 20 mM PIPES buffer containing 1 mM calcium chloride. To the solution, each of the additives shown in Table 2 was separately added, followed by lyophilization. The obtained lyophilizates were allowed to stand at room temperature for 60 minutes, and then stored at 37° C. for 1 week. Thereafter, the lyophilizates were dissolved to measure the enzyme activity. Table 2 shows the residual enzyme activity (%), relative to the enzyme activity immediately after lyophilization, which is taken as 100% residual activity.

TABLE 2

| | Additives | Residual activity (%) |
|---|---|---|
| 1 | BSA 45% | 72 |
| 2 | BSA 30% + α-cyclodextrin 30% | 82 |
| 3 | BSA 30% + malic acid 30% | 90 |

Table 2 shows that the combination of BSA and α-cyclodextrin or malic acid, which showed excellent effect in Example 1, improved the stability of the lyophilizates, even when using a buffer of a different composition.

As demonstrated in the above Examples, when (i) at least one compound selected from the group consisting of aspartic acid, glutamic acid, α-ketoglutaric acid, malic acid, α-ketogluconic acid, α-cyclodextrin and their salts and (ii) an albumin are present in a composition containing a PQQ-dependent glucose dehydrogenase, the enzyme composition is much more stable than conventional enzyme compositions.

What is claimed is:

1. A stable lyophilized PQQ-dependent glucose dehydrogenase composition consisting essentially of a PQQ-dependent glucose dehydrogenase together with (i) at least one compound selected from the group consisting of α-ketoglutaric acid, malic acid, α-ketogluconic acid, α-cyclodextrin and their salts, (ii) an albumin, (iii) a buffer, and (iv) a calcium ion or a calcium salt.

2. A method for stabilizing a PQQ-dependent glucose dehydrogenase, said method comprising (a) providing a PQQ-dependent glucose dehydrogenase and (b) forming a lyophilized composition consisting essentially of the PQQ-dependent glucose dehydrogenase together with (i) at least one compound selected from the group consisting of, α-ketoglutaric acid, malic acid, α-ketogluconic acid, α-cyclodextrin and their salts, (ii) an albumin, (iii) a buffer, and (iv) a calcium ion or a calcium salt.

3. A stable lyophilized PQQ-dependent glucose dehydrogenase composition consisting essentially of a PQQ-dependent glucose dehydrogenase together with (i) at least one compound selected from the group consisting of aspartic acid, α-ketoglutaric acid, malic acid, α-ketogluconic acid, α-cyclodextrin and their salts, (ii) an albumin, (iii) a buffer, and (iv) a calcium ion or a calcium salt.

4. The composition of claim 3, wherein aspartic acid or a salt thereof is present in the composition.

5. The composition of claim 3, wherein α-ketoglutaric acid or a salt thereof is present in the composition.

6. The composition of claim 3, wherein malic acid or a salt thereof is present in the composition.

7. The composition of claim 3, wherein α-ketogluconic acid or a salt thereof is present in the composition.

8. The composition of claim 3, wherein α-cyclodextrin or a salt thereof is present in the composition.

9. A method for stabilizing a PQQ-dependent glucose dehydrogenase, said method comprising (a) providing a PQQ-dependent glucose dehydrogenase and (b) forming a lyophilized composition consisting essentially of the PQQ-dependent glucose dehydrogenase together with (i) at least one compound selected from the group consisting of aspartic acid, α-ketoglutaric acid, malic acid, α-ketogluconic acid, α-cyclodextrin and their salts, (ii) an albumin, (iii) a buffer, and (iv) a calcium ion or a calcium salt.

10. The method of claim 9, wherein aspartic acid or a salt thereof is present in the composition.

11. The method of claim 9, wherein α-ketoglutaric acid or a salt thereof is present in the composition.

12. The method of claim 9, wherein malic acid or a salt thereof is present in the composition.

13. The method of claim 9, wherein α-ketogluconic acid or a salt thereof is present in the composition.

14. The method of claim 9, wherein α-cyclodextrin or a salt thereof is present in the composition.

* * * * *